United States Patent
Bok et al.

(10) Patent No.: US 6,562,866 B1
(45) Date of Patent: May 13, 2003

(54) METHOD FOR PREVENTING OR TREATING ELEVATED BLOOD LIPID LEVEL-RELATED DISEASES BY ADMINISTERING RUTIN AND QUERCETIN

(75) Inventors: Song-Hae Bok, Daejeon (KR); Tae-Sook Jeong, Daejeon (KR); Ki-Hwan Bae, Daejeon (KR); Yong-Bok Park, Daegu (KR); Myung-Sook Choi, Daegu (KR); Surk-Sik Moon, Gongju-shi (KR); Yong-Kook Kwon, Daejeon (KR); Eun-Sook Lee, Daejeon (KR); Byung-Hwa Hyun, Daejeon (KR); Yang-Kyu Choi, Daejeon (KR); Chul-Ho Lee, Daejeon (KR); Sae-Bom Lee, Daejeon (KR); Young-Bae Park, Seoul (KR); Hyo-Soo Kim, Seoul (KR)

(73) Assignee: Korea Research Institute of Bioscience and Biotechnology, Oeun-dong (KR)

( * ) Notice: Subject to any disclaimer, the term of this patent is extended or adjusted under 35 U.S.C. 154(b) by 69 days.

(21) Appl. No.: 09/649,322

(22) Filed: Aug. 28, 2000

Related U.S. Application Data

(62) Division of application No. 09/396,311, filed on Sep. 15, 1999, now abandoned.

(30) Foreign Application Priority Data

Sep. 15, 1998 (KR) .......................................... 98-37959

(51) Int. Cl.$^7$ ........................ A61K 31/352; A61P 9/10
(52) U.S. Cl. ...................... 514/456; 514/824; 514/27; 514/53; 424/439
(58) Field of Search .......................... 514/27, 53, 456, 514/824, 893; 424/439

(56) References Cited

PUBLICATIONS

CA 91: 122481, Voskresenskii Et Al, 1979.*
CA 103: 206002, Syrov Et Al, 1985.*

* cited by examiner

Primary Examiner—Edward J. Webman
(74) Attorney, Agent, or Firm—Katten Muchin Zavis Rosenman

(57) ABSTRACT

A method for treating or preventing an elevated blood lipid level-related disease in a mammal, which comprises administering thereto an effective amount of rutin, quercetin or a mixture thereof.

11 Claims, 6 Drawing Sheets

METHOD FOR PREVENTING OR TREATING ELEVATED BLOOD LIPID LEVEL-RELATED DISEASES BY ADMINISTERING RUTIN AND QUERCETIN

This application is a division of Ser. No. 09/396,311 filed Sep. 15, 1999 now abandoned.

FIELD OF THE INVENTION

The present invention relates to a method for preventing or treating elevated blood lipid level-related diseases such as hyperlipidemia, arteriosclerosis, angina pectoris, stroke and hepatic diseases in mammals, which comprises by administering thereto an effective amount of rutin and/or quercetin.

BACKGROUND OF THE INVENTION

It has been reported that blood lipids, especially cholesterols and triglycerides, are closely related to various kind of diseases such as coronary cardio-circulatory diseases, e.g., arteriosclerosis and hypercholesterolemia, and fatty liver. Cholesterol, a fatty steroid alcohol, is a blood lipid produced from saturated fat in the liver. Triglycerides are another type of blood lipids which are known to increase the risk of various diseases. It has also been reported that an elevated blood or plasma cholesterol level causes the deposition of fat, macrophages and foam cells on the wall of blood vessels, such deposit leading to plaque formation and then to arteriosclerosis (see Ross, R., *Nature*, 362, 801–809(1993)). One of the methods for decreasing the plasma cholesterol level is alimentotherapy to reduce the ingestion of cholesterol and lipids. Another method is to inhibit the absorption of cholesterol by inhibiting enzymes involved therein.

Acyl CoA-cholesterol-o-acyltransferase(ACAT) promotes the esterification of cholesterol in blood. Foam cells are formed by the action of ACAT and contain a large amount of cholesterol ester carried by low density lipoproteins. The formation of foam cells on the wall of artery increases with the ACAT activity, and, accordingly, an inhibitor of ACAT may also be an agent for preventing arteriosclerosis. Further, it has been reported that the blood level of LDL-cholesterol can be reduced by inhibiting the ACAT activity (see Witiak, D. T. and D. R. Feller (eds.), *Anti-Lipidemic Drugs: Medicinal, Chemical and Biochemical Aspects*, Elsevier, pp159–195 (1991))

Further, it has been reported that hypercholesterolemia can be treated effectively by reducing the rate of cholesterol biosynthesis through the inhibition of cholesterol ester transfer protein (CETP) which mediates the cholesterol transfers between the lipoproteins, or 3-hydroxy-3-methylglutaryl coenzyme A (HMG-CoA) reductase which mediates the synthesis of mevalonic acid, an intermediate in the biosynthesis of sterols or isoprenoids (see *Cardiovascular Pharmacology*, William W. Parmley and Kanu Chatterjee Ed., Wolfe Publishing, pages 8.6–8.7, 1994).

Therefore, numerous efforts have been made to develop medicines to inhibit HMG-CoA reductase; and, as a result, several compounds derived from Penicillium sp. and Aspergillus sp. have been commercialized. Specifically, Lovastatin® and Simvastatin® developed by Merck Co., U.S.A., and Pravastatin® developed by Sankyo Co., Japan, have been commercialized (see C. D. R. Dunn, *Stroke: Trends, Treatment and Markets*, SCRIPT Report, PJB Publications Ltd., 1995).

However, these medicines are very expensive and a long-term administration thereof is known to induce an adverse side effect to the central nervous system. Further, although Lovastatin® and Simvastatin® may reduce the plasma LDL cholesterol level by enhancing the activity of LDL receptor in the liver, they cause side effects such as increase in creatine kinase in the liver and rhabdomyloysis (see Farmer, J. A., et al., Baillers-clin. Endocrinol. Metal., 9, 825–847 (1995)). Accordingly, there has continued to exist a need to develop an inexpensive and non-toxic inhibitor of HMG-CoA reductase.

Another example of the elevated blood-lipid level-related disease is fatty liver. In particular, the excessive intake of fat-containing foods and alcohol causes fatty liver wherein a large amount of lipids is deposited in the liver tissue and the levels of serum GOT (glutamate-oxaloacetate transaminase), GPT (glutamate-pyruvate transaminase) and γ-GTP (γ-glutamyl transpeptidase) are elevated (see T. Banciu et al., *Med. Interne.*, 20, 69–71(1982); and A. Par et al., *Acta. Med. Acad. Sci. Hung.*, 33, 309–319(1976)).

Fat accumulates in the liver mainly in the form of triglycerides and fatty acids, and also to a minor extent in the form of cholesterol. Further, it has been reported that one of the major signs of fatty liver is high blood cholesterol and/or triglyceride contents. Therefore, fatty liver is closely related to the level of cholesterol and/or triglycerides in the blood.

Bioflavonoids are polyphenolic antioxidants which exist widely in the natural world, especially in vegetables, fruits, wine and the like. Hertog et al. have reported that the high uptake of rutin and quercetin may reduce the heart diseases-related death rate of old aged patients (see M. G. L. Hertog et al., Dietary antioxidant flavonoids and risk of coronary heart disease, Lancet. 342:1007–1011, 1993).

It has been reported that the bioflavonoids exhibit various useful pharmacological activities such as anti-inflammatory, capillary reinforcing, anti-oxidative, anti-cancer, anti-viral and anti-platelet aggregation activities (see O. Benavente-Garcia et al., Uses and properties of citrus flavonoids, *J. Agr. Food Chem.*, 45, 4506–4515, 1997). Rutin, a glycosylated quercetin, is decomposed to quercetin by the action of microorganisms and absorbed in the intestines (see C. Manach et al., Bioavailability, metabolism, and physiological impact of 4-oxo-flavonoids. Nutrition Research 16:517–544, 1996).

Representative bioflavonoids, which can be found in citruses, are listed in Table I.

TABLE I

| Citrus fruit | Bioflavonoids |
|---|---|
| Grapefruit | apigenin, dihydrokaempferol, eriodictyol, hesperetin, hesperidin, isorhamnetin, isosakuranetin, kaempferol, naringenin, naringin, neohesperidin, poncirin, quercetin, rutin |
| Lemon | apigenin, apigenin 7-rutinoside, chrysoeriol, diosmin, eriocitrin, hesperidin, isorhamnetin, limocitrin, limocitrol, luteolin 7-rutinoside, naringin, neohesperidin, poncirin, quercetin |
| Orange | auranetin, hesperidin, isosakuranetin 7-rutinoside, naringin, neohesperidin, nobiletin, rutin, sinensetin, tangeretin, vitexin |
| Tangerine | hesperidin, nobiletin, tangeretin |

Rutin is also known to be effective in treating high protein edema (see U.S. Pat. No. 5,096,887); and quercetin has anti-cancer and anti-viral activities (see Japanese Patent Laid-open Patent Publication No. 4-234320).

The present inventors have endeavored to develop a novel pharmacological use of bioflavonoids which are abundantly present in herbs, foodstuffs, vegetables and fruits. As a result, it has been discovered that rutin and quercetin are effective in treating or preventing elevated blood lipid level-related diseases. Specifically, they can greatly reduce plasma cholesterol level; prevent the activities of HMG-CoA reductase and ACAT; inhibit the accumulation of macrophage-lipid complex on the endothelial wall of an artery in a mammal; and prevent hepatic dysfunctions in a mammal.

SUMMARY OF THE INVENTION

Accordingly, it is an object of the present invention to provide a such as hyperlipidemia, arteriosclerosis, angina pectoris, stroke and hepatic diseases in a mammal, Accordingly, it is a primary object of the present invention to provide a method for treating or preventing an elevated blood lipid level-related disease in a mammal.

In accordance with one aspect of the present invention, there is provided a method for treating or preventing an elevated blood lipid level-related disease in a mammal, which comprises administering thereto an effective amount of rutin, quercetin or a mixture thereof.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1A:
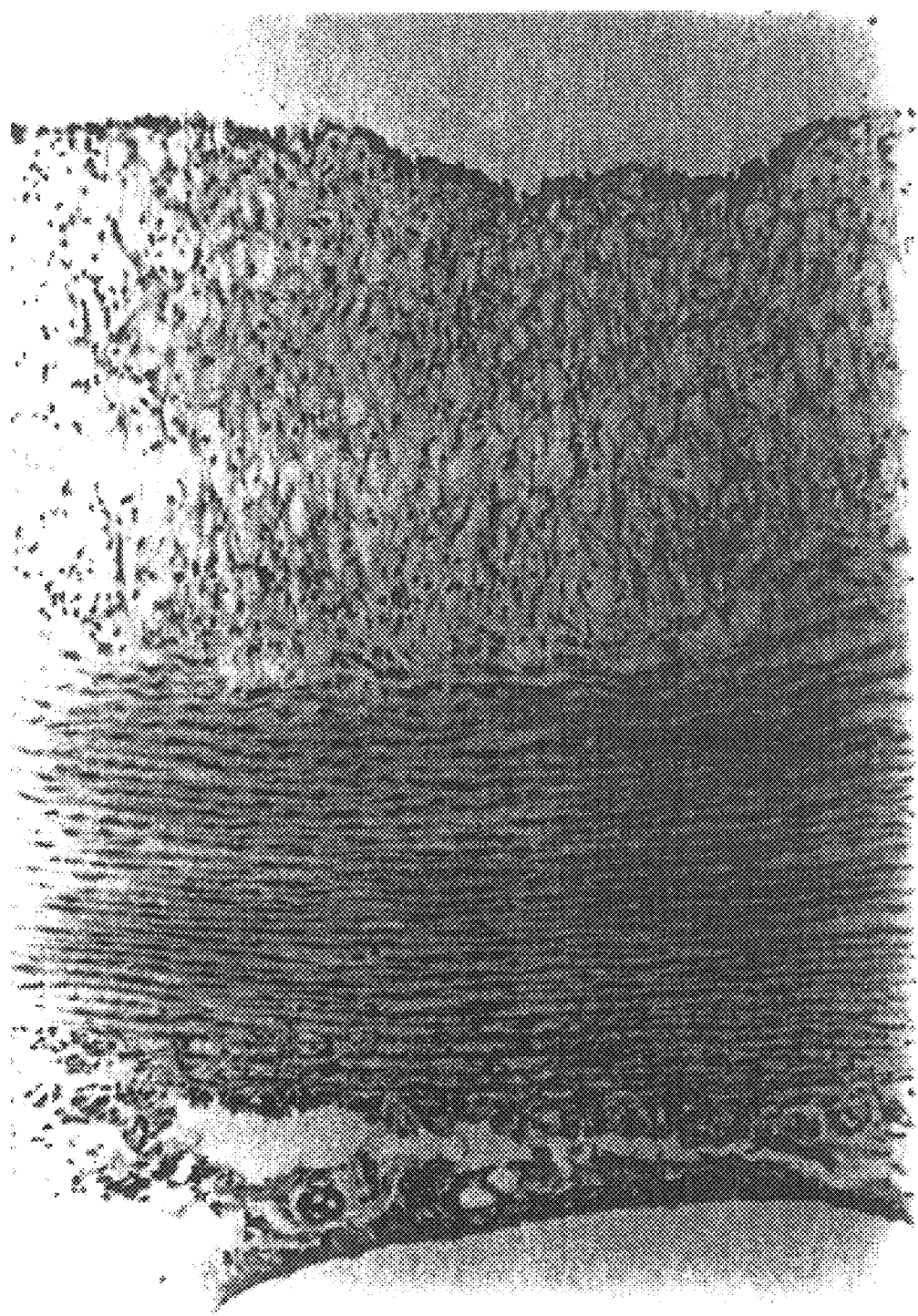
FIGS. 1A, 1B and 1C show the arterial endothelium of the rabbits administered with 1% cholesterol; 1% cholesterol plus 1 mg/kg Lovastatin®; and 1% cholesterol plus 0.1% rutin, respectively.

Throughout the specification, the term "blood lipid" designates a lipid present in blood. The blood lipid is represented by cholesterol and triglycerides carried in the blood.

The term "high or elevated level" of a blood lipid means a higher than normal level, the normal level varying with specific conditions of a patient, such as age, gender and body weight. A high level of blood lipid or glucose in ordinarily considered to be harmful to health.

The term "elevated blood lipid level-related disease" means a disease which is caused by a high or elevated level of blood lipid, and/or a disease whose symptoms include a high or elevated level of blood lipid. Examples of such a disease include hyperlipidemia, arteriosclerosis, angina pectoris, stroke, hepatic diseases such as fatty liver and the like.

Rutin ($C_{27}H_{30}O_{16}$, M.W. 610.51, glycosylated quercetin, see Merck Index 11th ed. (1989)) and quercetin ($C_{15}H_{10}O_7$, M.W. 302.23) may be extracted from various plants including vegetables such as lettuce and onion, fruits such as citrus, and grains such as buckwheat, or synthesized in accordance with the conventional process described by Zemplen, Bognar in *Ber.*, 1043 (1943) and Seka, Prosche, *Monatsh.*, 69, 284 (1936).

For example, rutin exist in buckwheat seeds, leaves, stems, flowers and sprouts in an amount ranging from 0.1 to 10 wt %. Thus, rutin and quercetin may be extracted from buckwheat by using a suitable solvent such as water or aqueous alcohol under a high temperature and pressure. Alternatively, buckwheat seeds, leaves, stems, flowers and/or sprouts may be allowed to stand overnight in an aqueous solution of $Ca(OH)_2$ or NaOH, and then crude rutin precipitates may be collected after neutralization. Further, dry powders of buckwheat seeds, leaves, stems and flowers may also be used. Generally, the content of rutin in leaves and stems of buckwheat is about 0.6% and that in buckwheat flower is about 3%.

Rutin and quercetin exert an inhibitory effect on elevated blood lipid level-related diseases such as hyperlipidemia, arteriosclerosis, angina pectoris, stroke and hepatic diseases as well as therapeutic effect. Further, in spite of their potent efficacies, quercetin or rutin exhibits no toxicity when it is orally administered to a mouse at a dose of 1,000 mg/kg and 160 mg/kg, respectively. Moreover, they exert no adverse effects on the liver function.

A pharmaceutical formulation may be prepared in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention contains the active ingredient in an amount ranging from 0.01 to 100 wt %, preferably, from 0.1 to 70 wt %. Further, the pharmaceutical composition of the present invention can be administered via various routes including oral, transdermal, subcutaneous, intravenous and intramuscular introduction. In case of human, a typical daily dose of the bioflavonoid may range from about 0.1 to 500 mg/kg body weight, preferably 0.5 to 100 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, rutin and quercetin can be advantageously incorporated in foods or, beverages for the purpose of treating or preventing hyperlipidemia, arteriosclerosis, angina pectoris, stoke and hepatic diseases. The foods or beverages may include meats; juices such as a vegetable juice (e.g., carrot juice and tomato juice) and a fruit juice (e.g., orange juice, grape juice, pineapple juice, apple juice and banana juice); chocolates; snacks; confectionery; pizza; food products made from cereal flour such as breads, cakes, crackers, cookies, biscuits, noodles and the likes; gums; dairy products such as milk, cheese, yogurt and ice creams; soups; broths; pastes, ketchups and sauces; teas; alcoholic beverages; carbonated beverages; vitamin complexes; and various health foods.

The content of the rutin and quercetin in a food or beverage may range from 0.01 to 10 wt %. In particular, the beverage according to the present invention may comprise 10 to 100 g of rutin, quercetin or a mixture thereof per 1000 ml of the beverage.

As described above, rutin or quercetin can be used as an effective, non-toxic pharmaceutical agent for treating or preventing elevated blood lipid level-related diseases such as hyperlipidemia, arteriosclerosis, angina pectoris, stroke and hepatic diseases.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1
Toxicity of Orally Administered Rutin 12 seven-week-old, specific pathogen-free ICR female mice, six female mice each weighing about 25 to 29 g and six male mice each weighing about 34 to 38 g, were kept under an environment of 22±1° C., 55±5% relative humidity and 12L/12D photoperiod. Fodder (Cheiljedang Co., mouse and rat fodder) and water were sterilized and fed to the mice.

Rutin purchased from Aldrich-Sigma Chemical Co. (St. Louis, Mo., U.S.A) was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter, the weight changes of the mice were recorded to examine the effect of rutin. Further, on the 10th day, the mice were sacrificed and the internal organs were visually examined.

All the mice were alive at day 10 and rutin showed no toxicity at a dose of 1,000 mg/kg. The autopsy revealed that the mice did not develop any pathological abnormality, and no weight loss was observed during the 10 day test period. Accordingly, it was concluded that rutin is not toxic when orally administered to an animal.

EXAMPLE 2
Effect of Rutin and Quercetin on Plasma Cholesterol, HDL-cholesterol and Neutral Lipid Levels
(Step 1) Administration of Rutin and Quercetin to Rats 30 three-week-old white Sprague-Dawley rats (Taihan laboratory animal center, Korea), each weighing about 90 to 110 g, were evenly divided into three dietary groups by a randomized block design. The rats of the three groups were fed with three different high-cholesterol diets, i.e., AIN-76 laboratory animal diet (ICN Biochemicals, Cleveland, Ohio, U.S.A.) containing 1% cholesterol (Control group), 1% cholesterol plus 0.1% rutin (Rutin group) and 1% cholesterol plus 0.1% quercetin (Quercetin group), respectively. The compositions of the diets fed to the three groups are shown in Table II.

TABLE II

| Dietary group Component | Control group (n = 10) | Rutin group (n = 10) | Quercetin group (n = 10) |
|---|---|---|---|
| Casein | 20 | 20 | 20 |
| D,L-methionine | 0.3 | 0.3 | 0.3 |
| Corn starch | 15 | 15 | 15 |
| Sucrose | 49 | 48.9 | 48.9 |
| Cellulose powder*[1] | 5 | 5 | 5 |
| Mineral mixture*[1] | 3.5 | 3.5 | 3.5 |
| Vitamin mixture*[1] | 1 | 1 | 1 |
| Choline citrate | 0.2 | 0.2 | 0.2 |
| Corn oil | 5 | 5 | 5 |
| Cholesterol | 1 | 1 | 1 |
| Rutin*[2] | — | 0.1 | — |
| Quercetin*[2] | — | — | 0.1 |
| Total | 100 | 100 | 100 |

*[1]Purchased from TEKLAD premier Co. (Madison, WI, U.S.A.)
*[2]Purchased from Sigma Chemical Co. (St. Louis, MO, U.S.A.)

The rats were allowed to feed freely on the specified diet together with water for six weeks, the ingestion amount was recorded daily and the,rats were weighed every 7 days, and then the record was analyzed. All rats showed a normal growth rate and there was observed no significant difference among the two groups in terms of the feed ingestion amount and the weight gain.

(Step 2) Determination of Total Cholesterol, HDL-cholesterol and Neutral Lipid Content in Blood The effects of administering rutin or quercetin to rats on the plasma cholesterol and neutral lipid content were determined as follows.

The rats of the dietary groups obtained in Step 1 were sacrificed and blood samples were taken therefrom. The blood was allowed to stand for 2 hours and centrifuged at 3,000 rpm for 15 minutes and the supernatant was separated and stored in a deep freezer before use. The chemical analysis of blood was carried out by employing a blood chemical analyzer (CIBA Corning 550 Express, USA) to determine the changes in total cholesterol, HDL-cholesterol and triglyceride levels. The result is shown in Table III.

TABLE III

| | Group | | |
|---|---|---|---|
| Lipid Conc. | Control group | Rutin group | Quercetin group |
| Total-C (mg/dl) | 135 ± 6 | 107 ± 6 | 95 ± 5 |
| HDL-C (mg/dl) | 38 ± 2 | 36 ± 2 | 41 ± 3 |
| TG (mg/dl) | 98 ± 5 | 78 ± 3 | 81 ± 4 |
| $\dfrac{\text{HDL-C}}{\text{Total-C}}$ (%) | 28 | 33 | 43 |

* Total-C: Total-cholesterol
* HDL-C: HDL-cholesterol
* TG: Triglyceride

As can be seen from Table III, the total plasma cholesterol level is reduced by 21% and 30% in the rutin and quercetin groups, respectively, as compared with that of the control group. The JDL-C/Total/C ratio is increase by 18% and 54% in the rutin and quercetin groups, respectively, as compared with that of the control group. Further, the neutral lipid content is reduced by 20% and 17% in the rutin and quercetin groups, respectively, as compared with that of the control group.

EXAMPLE 3
Activities of Rutin and Quercetin in ACAT Inhibition
(Step 1) Preparation of Microsomes To determine the effect of feeding rutin to rats on the activity of ACAT, microsomes were separated from the liver tissues to be used as an enzyme source.

1 g each of the livers taken from each group of rats of Example 2 was homogenized in 5 ml of homogenization medium (0.1 M $KH_2PO_4$, pH 7.4, 0.1 mM EDTA and 10 mM β-mercaptoethanol). The homogenate was centrifuged at 3,000×g for 15 min. at 4° C. and the supernatant thus obtained was centrifuged at 15,000×g for 15 min. at 4° C. to obtain a supernatant. The supernatant was put into an ultracentrifuge tube (Beckman) and centrifuged at 100,000×g for 1 hour at 4° C. to obtain microsomal pellets, which were then suspended in 3 ml of the homogenization medium and centrifuged at 100,000×g for 1 hour at 4° C. The pellets thus obtained were suspended in 1 ml of the homogenization medium. The protein concentration of the resulting suspension was determined by Lowry's method and then adjusted to 4 to 8 mg/ml. The resulting suspension was stored in a deep freezer (Biofreezer, Forma Scientific Inc.).

(Step 2) ACAT Assay 6.67 µl of 1 mg/ml cholesterol solution in acetone was mixed with 6 µl of 10% Triton WR-1339 (Sigma Co.) in acetone and, then, acetone was removed from the mixture by evaporation under a nitrogen; flow. Distilled water was added to the resulting mixture to adjust the concentration of cholesterol to 30 mg/ml.

Added to 10 µl of the resulting aqueous cholesterol solution were 10 µl of 1 M $KH_2PO_4$ (pH 7.4), 5 µl of 0.6 mM bovine serum albumin (BSA), 10 µl of microsome solution obtained in (Step 1) and 55 µl of distilled water (total 90 µl). The mixture was pre-incubated in a water bath at 37° C. for 30 min. 10 µl of $(1-^{14}C)$ oleyl-CoA solution (0.05 µCi, final concentration: 10 µM) was added to the pre-incubated mixture and the resulting mixture was incubated in a water bath at 37° C. for 30 min. Added to the mixture were 500 µl of isopropanol:heptane mixture (4:1 (v/v)), 300 µl of heptane and 200 µl of 0.1 M $KH_2PO_4$ (pH 7.4), and the mixture was mixed vigorously using a vortex mixer and then allowed to stand at a room temperature for 2 min.

200 µl of the resulting supernatant was put in a scintillation bottle and 4 ml of scintillation fluid (Lumac) was added thereto. The mixture was assayed for radioactivity with 1450 Microbeta liquid scintillation counter (Wallacoy, Finland). ACAT activity was calculated as picomoles of cholesteryl oleate synthesized per min. per mg protein (pmoles/min/mg protein). The result is shown in Table IV.

TABLE IV

| Group | % Inhibition on ACAT activity |
| --- | --- |
| Control group | 0 |
| Rutin group | 25 |
| Quercetin group | 20 |

As can be seen from Table IV, ACAT activities observed in the rutin and quercetin groups are lower than that of the control group by 20–25%.

EXAMPLE 4
Activities of Rutin and Quercetin in HMG-CoA Reductase Inhibition

In order to determine the activity of HMG-COA reductase, Hulcher's method was employed after some modification (see *J. Lipid Res.*, 14, 625–641(1973)). In this method, the concentration of the coenzyme-A (CoA-SH), which is produced when HMG-CoA is reduced to a mevalonate salt by the action of HMG-CoA reductase, is determined by spectroscopy and the activity of HMG-CoA reductas e is calculated therefrom.

(Step 1) Preparation of Microsomes 3g of liver tissue taken from each group of rats of Example 2 was washed successively with 100 ml of a cold saline (0.15M NaCl) and 100 ml of a cold buffer solution A (0.1M triethanolamine, HCl/0.2M EDTA/2 mM dithiothreitol (DTT)). The cold buffer solution A was added to the liver tissue in an amount of 2 ml per 1 g of the liver tissue and the mixture was homogenized with a homogenizer. The homogenate was centrifuged at 15,000×g for 15 minutes, and then, the supernatant was ultracentrifuged at 100,000×g for 60 minutes to obtain microsomal precipitates. The precipitates thus obtained was washed with a cold buffer solution A and kept in a 1.5 ml tube at −70° C.

(Step 2) HMG-CoA Reductase Activity Assay

The reaction substrates used in HMG-CoA reductase activity assay were as follows: i) buffer solution B: 0.1M triethanolamine, HCl/0.02M EDTA (pH7.4), ii) HMG-CoA solution: 150 µmoles/culture medium, and iii) NADPH solution: 2 µmoles/culture medium.

The suspension (microsome) was mixed with the reaction substrate and the mixture was placed in a centrifugation tube and reacted at 37° C. for 30 minutes. The reaction mixture was treated with 20 µl of 0.01M sodium arsenous and allowed to stand for 1 minute, and then it was reacted with 100 µl of citrate buffer solution (2M citrate/3% sodium tungstate, pH 3.5) at 37° C. for 10 minutes followed by centrifugation at 25,000×g for 15 minutes to remove protein. 1 ml of the supernatant thus obtained was transferred into a tube with a cap and added thereto were 0.1 ml of 2M tris-HCl solution (pH 10.6) and 0.1 ml of 2M tris-HCl solution (ph 8.0) to adjust the pH of the reactant to 8.0.

Then, the reactant was mixed with 20 µl of DTNB buffer solution (3mM DTNB/0.1M triethanolamine/0.2M EDTA, pH 7.4) and the absorbance of the mixture was determined at 412 nm to calculate the amount of CoA-SH (activity of HMG-CoA reductase activity).

The extents of inhibition of HMG-CoA reductase activity by rutin and quercetin were calculated based on the above result. The result is shown in Table V.

TABLE V

| Group | Inhibition of HMG-CoA reductase activity (%) |
| --- | --- |
| Control | 0 |
| Rutin | 40 |
| Quercetin | 30 |

As can be seen in Table IV, the HMG-CoA reductase activities observed with the rutin and quercetin-fed rat groups are lower than that of the control group by 30–40%.

EXAMPLE 5
Effect of Administration of Rutin to a Human on Plasma Lipid Metabolism Two men in their mid-fifties were administered with a daily oral dose of 1omg/kg of rutin in the form of a capsule for 60 days. The plasma cholesterol and neutral lipid (triglyceride) contents were determined before and after the administration.

The plasma cholesterol and neutral lipid contents were reduced by the rutin administration by 25% and 20%, respectively.

EXAMPLE 6

Inhibition of Arteriosclerosis (Step 1) Administration of Rutin to Rabbits 24 three-month-old New Zealand White rabbits (Yeonam Horticulture and Animal Husbandry College, Korea), each weighing about 2.5 to 2.6 kg, were raised under a condition of temperature 20±2° C., relative humidity 55±5%, and photoperiod 12L/12D. The rabbits were divided into 4 groups and 4 groups of rabbits were fed with 4 different diets, i.e., RC4 diet (Oriental Yeast Co., Japan) containing 1% cholesterol (Control group); 1% cholesterol plus 1 mg/kg Lovastatin® (Merck, U.S.A.) (Comparative group); 1% cholesterol plus 0.1% rutin; 1% cholesterol plus 0.1% quercetin, respectively. RC4 diet comprises 7.6% moisture, 22.8% crude protein, 2.8% crude fat, 8.8% crude ash, 14.4% crude cellulose and 43.6% soluble nitrogen-free substances. Rutin and quercetin were purchased from Sigma Co. (St. Louis, Mo.).

The rabbits were fed for 6 weeks while being allowed free access to the diets and water.

(Step 2) Chemical Analysis of Blood

After six weeks, the rabbits were anesthetized with an intramuscular injection of ketamine (50 mg/kg) in the femoral region and sacrificed. A blood sample was taken from the heart of each rabbit, allowed to stand for 2 hours and centrifuged at 3,000 rpm for 15 minutes and the supernatant serum was separated and stored in a freezer before use.

The chemical analysis of blood was carried out by employing a blood chemical analyzer (CIBA Corning 550 Express, USA) to determine the changes in GOT, GPT, γ-GTP, total cholesterol and triglyceride levels. The results are shown in Table VI.

(Step 3) Analysis for Fatty Streak in the Main Artery

The chest of each of the rabbits sacrificed in Step 2 was incised. The downward portion of the main artery from the site 1 cm above the aortic valve was cut out in a length of about 5 cm and the fat surrounding the main artery was removed. The main artery was incised in the middle along the longitudinal axis and pinned to a dish. The moist artery was photographed and, then, the staining of fatty streaks was carried out in accordance with the method of Esper, E., et al. (*J. Lab. Clin. Med.*, 121, 103–110 (1993)) as follows.

A part of the incised main artery was washed three times with anhydrous propylene glycol for 2 min and stained for 30 min. with a saturated solution of Oil Red O (ORO, Sigma Co.) dissolved in propylene glycol. Thereafter, the artery was washed twice with 85% propylene glycol for 3 min. to remove remaining staining solution and, then washed with physiological saline. The artery was photographed and the photograph was traced. The area of stained region (fatty streak region) was determined with an image analyzer (LEICA, Q-600, Germany) and its proportion (%) to the total arterial area was calculated. The result is shown in Table VI.

Figure 1B:
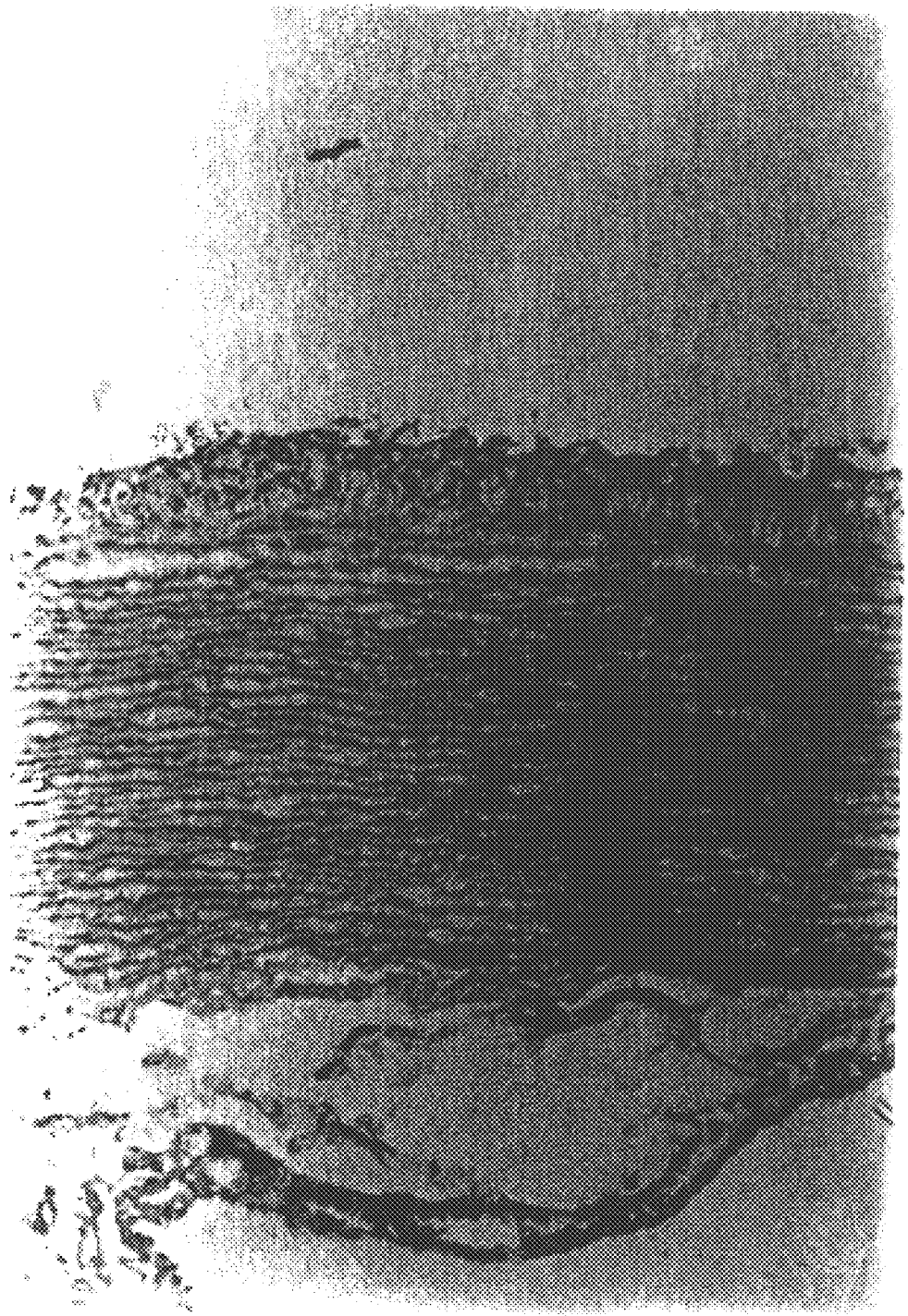
Figure 1C:
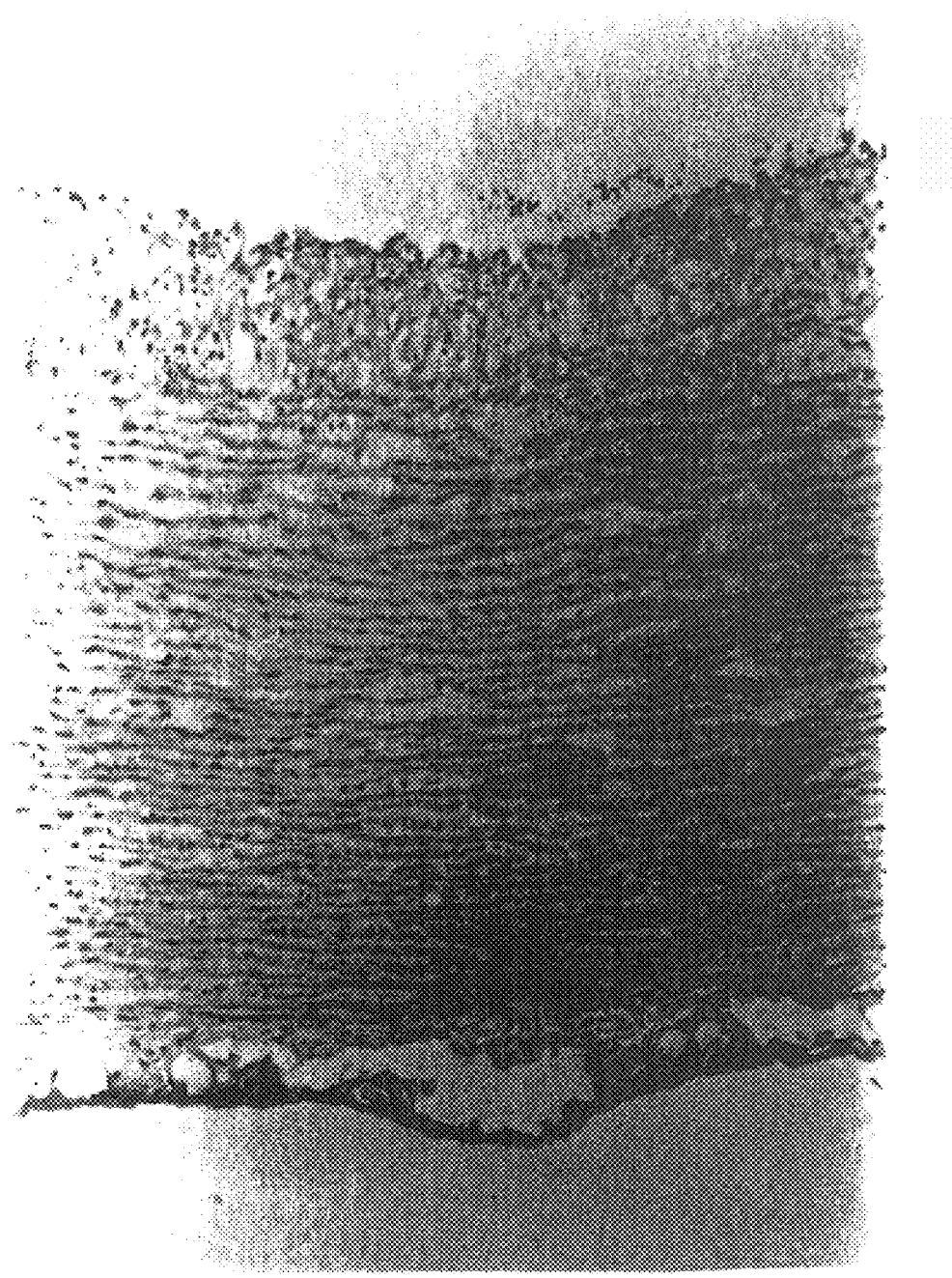

FIGS. 1A, 1B and 1C show the arteries of the rabbits administered with 1% cholesterol (Control group); 1% cholesterol plus 1 mg/kg Lovastatin® (Comparative group); and 1% cholesterol plus 0.1% rutin (Rutin group), respectively. As shown in FIGS. 1A, 1B and 1C, a thick layer of macrophage-lipid complex was observed on the arterial endothelium of the rabbit administered with 1% cholesterol, while no or very thin layers of macrophage-lipid complex were observed on the arterial endothelia of the rabbits administered with 1% cholesterol plus 1 mg/kg Lovastatin® and 1% cholesterol plus 0.1% rutin, respectively.

Accordingly, it is concluded that the rutin composition of the present invention strongly inhibits the deposition of macrophages on the arterial endothelium.

(Step 4) Histologic Observation of the Organs

Portions of the main artery, heart, lung, liver, kidney and muscle were taken from each of the rabbits sacrificed in Step 2 and visually examined to confirm that no pathogenic abnormality was found. One half of each portion of the organs was deep freezed and the other half was fixed in 10% neutral buffered formalin for more than 24 hours. The fixed organ. piece was washed sufficiently with tap water, dehydrated stepwise with 70%, 80%, 90% and 100% ethanol and, then, embedded in paraffin by employing SHANDON®, Histocentre 2, USA. The embedded organ piece was sectioned in 4 μm thickness with a microtome (LSICA, RM2045, Germany) and stained with hematoxylin and eosin. The stained organ specimen was made transparent with xylene, mounted with permount, and then observed under a microscope to look for the presence of lesions. No lesion was observed in any of the organ specimen.

EXAMPLE 7

Prevention of Hepatic Diseases

In order to evaluate the effects of feeding a high cholesterol diet with rutin and quercetin on liver tissues, the liver specimens taken from the sacrificed rabbit in Step 2 of Example 6 were treated in accordance with the procedure disclosed in Fogt F. and Nanji A., Toxicology and Applied Pharmacology, 136, 87–93, 1996; and Keegan A., et al., Journal of Hepatology 23: 591–600, 1995, and observed under a microscope to be classified into four grades, i.e., 1+(0–25%), 2+(26–50%), 3+(51–75), 4+(76–100%) based on the proportion of abnormal fat-containing cells around the central vein in the liver acinus. The result is shown in Table VI.

Figure 2A:
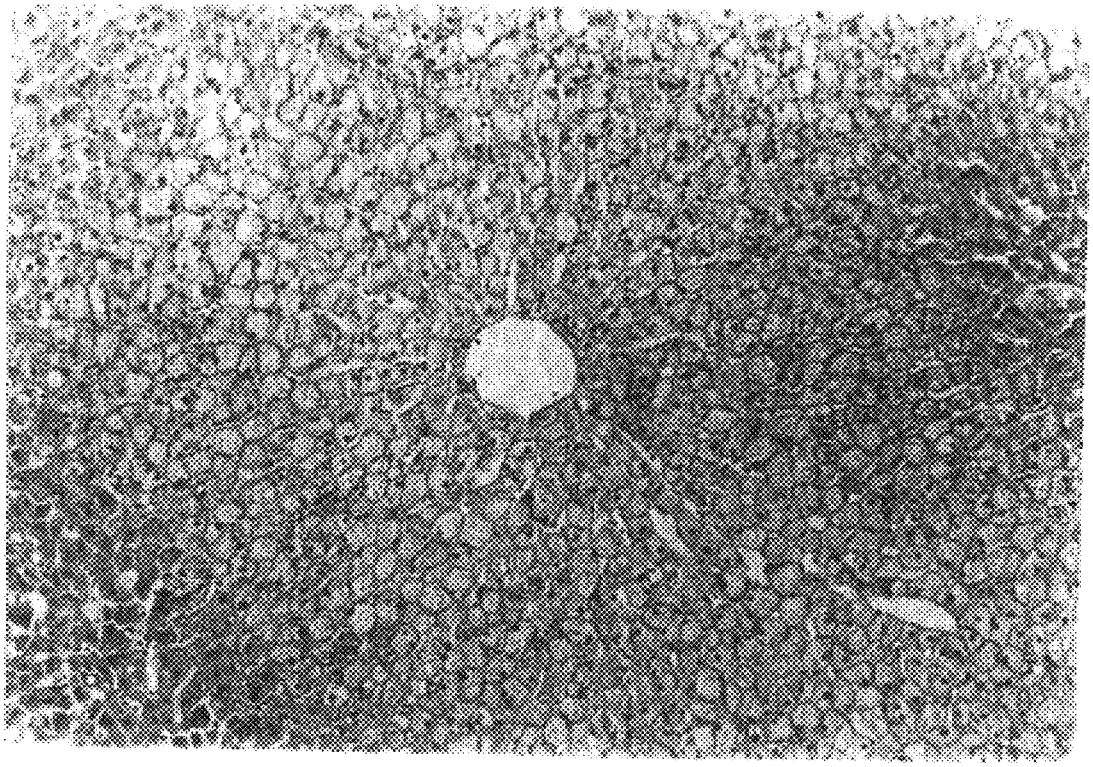
FIGS. 2A, 2B and 2C present the microscopic features of the livers of the rabbits administered with 1% cholesterol; 1% cholesterol plus 1 mg/kg Lovastatin ; and 1% cholesterol plus 0.1% rutin, respectively.
Figure 2B:
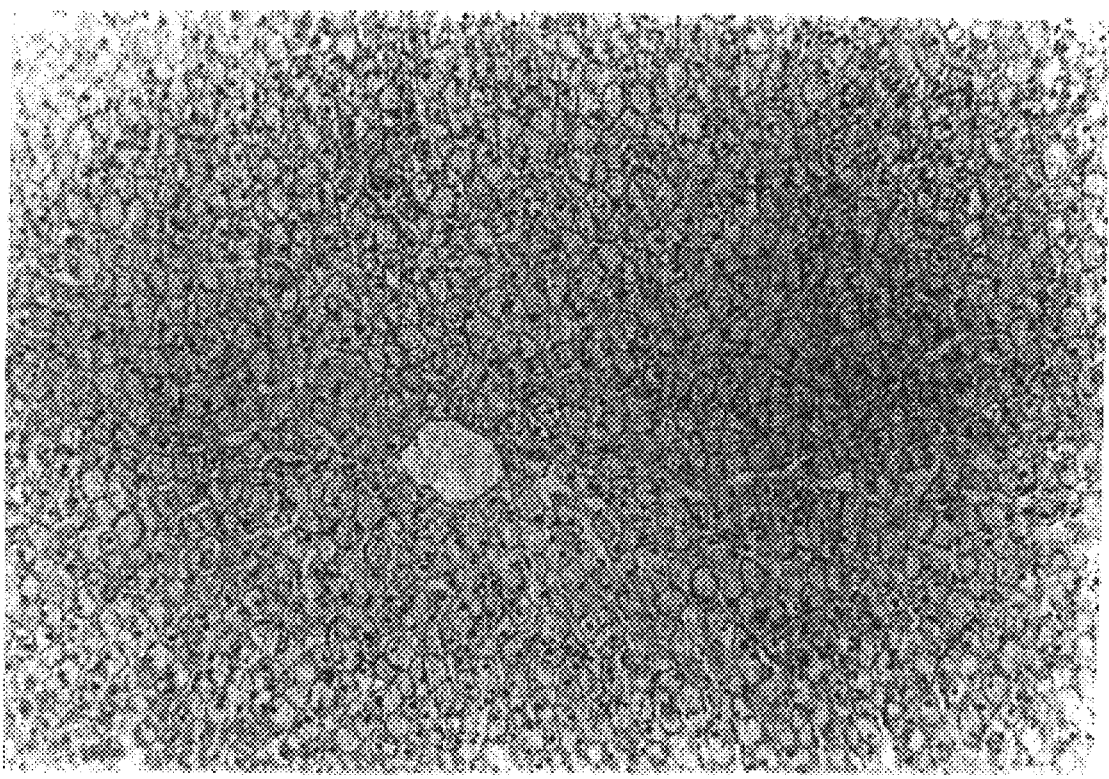
Figure 2C:
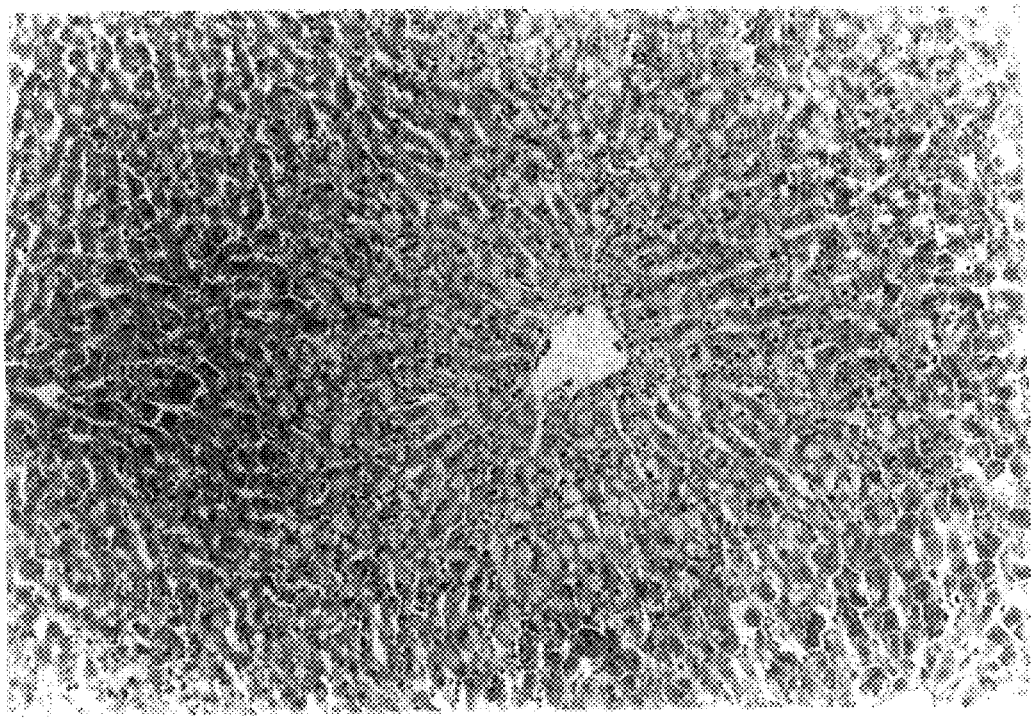

FIGS. 2A, 2B and 2C present the microscopic features of the livers of the rabbits administered with 1% cholesterol; 1% cholesterol plus 1 mg/kg Lovastatin®; 1% and cholesterol plus 0.1% rutin, respectively. In FIGS. 2A and 2B, many cells containing excessive fat were observed around the central vein. In contrast, almost all liver cells are of a normal shape in FIG. 2C, which suggested that rutin can significantly inhibit the formation of fatty liver.

As can be seen from the above, the administration of rutin or quercetin can improve lipid metabolism in rabbit and liver function and inhibit the plaque formation in the endothelium of the main artery and formation of fatty liver as shown in Table VI. The results were tested by student t-test by using Microsoft excel (version 7.0) program.

TABLE VI

|  | Group | | | | | | |
| --- | --- | --- | --- | --- | --- | --- | --- |
|  | Total-C (mg/dl) | TG (mg/dl) | GOT (IU/l) | GPT (IU/l) | γ-GTP (IU/l) | A (%) | B |
| Control | 1143.2 (±260.6) | 55.8 (±38.2) | 76.8 (±8.2) | 65.2 (±9) | 4.2 (±1) | 35 (±14) | 3.2 + (±0.3) |

TABLE VI-continued

|  | Group | | | | | | |
| --- | --- | --- | --- | --- | --- | --- | --- |
|  | Total-C (mg/dl) | TG (mg/dl) | GOT (IU/l) | GPT (IU/l) | γ-GTP (IU/l) | A (%) | B |
| Lovastatin ® | 1209.5 (±263.3) | 65.6 (±16.9) | 125.6 (±18) | 72.5 (±9.3) | 12.3 (±0.8) | 5 (±4) | 3.4 + (±0.5) |
| Rutin | 798.2 (±430.6) | 35.3 (±18.4) | 87.0 (±19.7) | 33.9 (±10) | 1.92 (±1.3) | 10 (±5) | 2.75 + (±0.3) |
| Quercetin | 820.0 (±270) | 30.0 (±12) | 80 (±15) | 30 (±8.1) | 2.5 (±1) | 8 (±3) | 2.6 + (±0.4) |

\* Total-C: Total-cholesterol
\* TG: Triglyceride
A: Proportion (%) of fatty streak region to the total arterial area
B: Proportion of abnormal fat-containing cells As can be seen from Table VI, administration of rutin and quercetin lowers total plasma cholesterol and neutral lipid levels by 30% and 44–45%, respectively, as compared to the comparative group. Especially, rutin and quercetin are more effective in reducing total plasma cholesterol and neutral lipid levels than Lovastatin®.

EXAMPLE 8

Extraction of Rutin

Ca(OH)$_2$ was added to buckwheat seeds, leaves or flowers to pH 10 to 12.0 and the mixture was allowed to stand overnight. The mixture was adjusted to pH 6 to 7 and the resulting precipitate was recovered to obtain a crude rutin (purity: 40 to 50%).

Alternatively, 100 g each of buckwheat leaves and flowers was extracted with 500 ml of 70% ethanol at 60° C. for 5 hours. The extracts thus obtained were filtered. The resulting extracts had 0.6% (leaves, stems) and 4% (flowers) of rutin, respectively.

Buckwheat seeds, leaves, stems and flowers were dried at a room temperature and then powdered.

Further, buckwheat seeds steeped in water were placed in a vessel and cultivated under a constant moisture condition until the size of the spouts became 1 to 10 cm. The sprouts thus obtained were powdered or extracted as described above.

A medicine or health food containing the rutin powder or extract thus obtained may be prepared in accordance with a conventional method.

EXAMPLE 9

Effect of Administration of Rutin to a Human

Two men in their mid-fifties were administered with a daily oral dose of log of rutin in the form of a buckwheat flower powder suspended in water for 60 days. The plasma cholesterol and neutral lipid contents were determined before and after the administration.

The plasma cholesterol and neutral lipid contents were reduced by the above treatment by 25% and 20%, respectively.

Accordingly, it is believed that when the rutin is administered in the form of a buckwheat flower powder, the inhibition of arteriosclerosis and hyperlipidemia can be obtained.

Formulation 1: Preparation of Pharmaceutical Formulation

Hard gelatin capsules were prepared using the following ingredients:

|  | Quantity (mg/capsule) |
| --- | --- |
| Active ingredient (rutin, quercetin or mixture thereof) | 200 |
| Vitamin C | 50 |
| Lactose (carrier) | 150 |
| Total | 400 mg |

Formulation 2: Foods Containing Rutin or Quercetin

Foods containing rutin or quercetin were prepared as follows.

(1) Preparation of tomato ketchup and sauce

A buckwheat powder having a size ranging from 100 to 200 μm was added to a tomato ketchup or sauce in a sufficient amount to obtain a health-improving tomato ketchup or sauce containing 0.01 to 10 wt % of rutin.

Alternatively, the buckwheat extract obtained in Example 8 was added to a tomato ketchup or sauce to obtain a health-improving tomato ketchup or sauce containing 0.01 to 10 wt % of rutin.

(2) Preparation of foods containing wheat flour

A buckwheat powder was added to wheat flour in a sufficient amount to obtain a wheat flour mixture containing 0.01 to 10 wt % of rutin, and breads, cakes, cookies, crackers and noodles were prepared by using the mixture to obtain health-improving foods.

Alternatively, these foods were prepared by using a wheat flour mixture containing 0.01 to 10 wt % of rutin in the form of the buckwheat extract obtained in Example 8.

(3) Preparation of soups and gravies

A buckwheat powder was added to soups and gravies in a sufficient amount to obtain health-improving soups and gravies containing 0.01 to 10 wt % of rutin.

Alternatively, these foods were prepared by using the buckwheat extract obtained in Example 8.

(4) Preparation of ground beef

A buckwheat powder was added to ground beef in a sufficient amount to obtain health-improving ground beef containing 0.01 to 10 wt % of rutin. Alternatively, these foods were prepared by using the buckwheat extract obtained in Example 8.

(5) Preparation of dairy products

A buckwheat powder was added to milk in a sufficient amount to obtain milk containing 0.01 to 10 wt % of rutin, and various dairy products such as butter and ice cream were prepared therefrom.

Alternatively, these foods were prepared by using the buckwheat extract obtained in Example 8.

In case of a cheese preparation, a buckwheat powder or extract was added to coagulated milk protein; and, in case of a yogurt preparation, a buckwheat powder or extract was added to coagulated milk protein obtained after the fermentation.

Formulation 3: Beverages Containing Rutin (1) Preparation of vegetable juice 10 to 100 g of the buckwheat powder or extract obtained in Example 8 was added to 1000 ml of a vegetable juice to obtain a health-improving vegetable juice.

(2) Preparation of fruit juice 10 to 100 g of the buckwheat powder or extract obtained in Example 8 was added to 1000 ml of fruit juice to obtain a health-improving fruit juice.

Formulation 4: Health Foods Containing Rutin

A health food was prepared by mixing the following ingredients and tabletting the mixture.

|  | Quantity (wt/wt %) |
| --- | --- |
| Ginseng powder or extract | 50% |
| rutin, quercetin or mixture thereof | 30% |
| Sweetener and flavor | 20% |
| Total | 100% |

While the invention has been described with respect to the above specific embodiments, it should be recognized that various modifications and changes may. be made to the invention by those skilled in the art which also fall within the scope of the invention as defined by the appended claims.

What is claimed is:

1. A method for inhibiting the activity of acyl CoA-cholesterol-o-acyltransferase(ACAT) in a mammal, which comprises administering thereto an effective amount of rutin, quercetin or a mixture thereof.

2. The method of claim 1, wherein the mammal is human.

3. The method of claim 1, wherein the rutin, quercetin or a mixture thereof is administered in the form of a pharmaceutical composition containing an effective amount of rutin, quercetin or a mixture thereof and pharmaceutically acceptable excipients, carriers or diluents.

4. The method of claim 1, wherein the effective amount of the rutin, quercetin or a mixture thereof ranges from 0.1 to 500 mg/kg of body weight/day.

5. The method of claim 1, wherein the rutin, quercetin or a mixture thereof is a ministered in the form of a health improving food composition containing rutin, quercetin or a mixture thereof in an amount ranging from 0.01 to 10 wt %.

6. The method of claim 5, wherein the rutin is added in the form of a powder or an extract from a buckwheat seed, sprout, flower, leaf or stem.

7. The method of 5, wherein the food is meat, chocolate, snack, confectionery, pizza, a food product made from cereal flour, gums, dairy products, soups, broths, pastes, ketchups, sauces, vitamin complexes, or health food.

8. The method of claim 7, wherein the food product made from cereal flour is bread, cake, cracker, cookie, biscuit or noodle.

9. The method of claim 7, wherein the dairy product is milk, ice cream, cheese or yogurt.

10. The method of claim 1, wherein the rutin, quercetin or a mixture thereof is administered in the form of a health improving beverage composition containing rutin, quercetin or a mixture thereof in an amount ranging from 0.01 to 10 wt %.

11. The method of claim 10, wherein the beverage is a vegetable juice, fruit juice, tea, alcoholic beverage or carbonated beverage.

* * * * *